United States Patent
Chen et al.

(10) Patent No.: US 11,259,997 B2
(45) Date of Patent: Mar. 1, 2022

(54) DENTAL SELF-ADHESIVE RESIN CEMENT

(71) Applicant: Bisco Inc., Schaumburg, IL (US)

(72) Inventors: Liang Chen, Hoffman Estate, IL (US);
Byoung In Suh, Oak Brook, IL (US);
Hong Shen, Hoffman Estate, IL (US);
Christine Gleave, Lewisburg, PA (US)

(73) Assignee: BISCO Inc., Schaumburg, IL (US)

( * ) Notice: Subject to any disclaimer, the term of this patent is extended or adjusted under 35 U.S.C. 154(b) by 0 days.

(21) Appl. No.: 15/702,674

(22) Filed: Sep. 12, 2017

(65) Prior Publication Data

US 2018/0078465 A1    Mar. 22, 2018

Related U.S. Application Data

(60) Provisional application No. 62/397,711, filed on Sep. 21, 2016.

(51) Int. Cl.
| | |
|---|---|
| *A61K 6/889* | (2020.01) |
| *A61K 6/836* | (2020.01) |
| *A61K 6/851* | (2020.01) |
| *C04B 28/04* | (2006.01) |
| *C04B 7/02* | (2006.01) |
| *C04B 14/00* | (2006.01) |
| *C04B 26/06* | (2006.01) |
| *C04B 111/00* | (2006.01) |

(52) U.S. Cl.
CPC .............. *A61K 6/889* (2020.01); *A61K 6/836* (2020.01); *A61K 6/851* (2020.01); *C04B 7/02* (2013.01); *C04B 14/005* (2013.01); *C04B 26/06* (2013.01); *C04B 28/04* (2013.01); *C04B 2111/00112* (2013.01); *C04B 2111/00836* (2013.01)

(58) Field of Classification Search
None
See application file for complete search history.

(56) References Cited

U.S. PATENT DOCUMENTS

| | | | |
|---|---|---|---|
| 5,508,342 A | 4/1996 | Antonucci | |
| 5,601,640 A | 2/1997 | Anstice | |
| 5,814,681 A | 9/1998 | Hino | |
| 8,129,444 B2 | 3/2012 | Hecht | |
| 8,785,518 B2 | 7/2014 | Suh | |
| 9,289,359 B2 | 3/2016 | Burtscher | |
| 2002/0045678 A1 | 4/2002 | Lopez | |
| 2007/0197682 A1* | 8/2007 | Jia | A61K 6/0023 523/116 |
| 2008/0058442 A1† | 3/2008 | Hermansson | |
| 2008/0318190 A1 | 12/2008 | Suh | |
| 2009/0018234 A1* | 1/2009 | Tokui | A61K 6/0835 523/116 |
| 2010/0240795 A1* | 9/2010 | Burtscher | A61K 6/0023 523/116 |
| 2012/0115109 A1† | 5/2012 | Chen | |
| 2013/0266915 A1* | 10/2013 | Tsuruta | A61K 6/75 433/226 |
| 2013/0274426 A1* | 10/2013 | Sugiura | A61K 6/083 526/123.1 |
| 2014/0161901 A1† | 6/2014 | Lee | |

FOREIGN PATENT DOCUMENTS

WO    2011080573    7/2011

OTHER PUBLICATIONS

Evonik Industries, Aerosil—Fumed Silica: Technical Overview, available online at: https://www.aerosil.com/sites/lists/RE/DocumentsSI/Technical-Overview-AEROSIL-Fumed-Silica-EN.pdf; accessed on Nov. 2, 2017, Dec. 31, 2015 (Dec. 31, 2015), p. 37.

Whitesides et al, Acid-base interactions in wetting, Journal of Adhesion Science and Technology, Jan. 31, 1991 (Jan. 31, 1999), p. 57-69, vol. 5.

International Search Report and Written Opinion of the International Searching Authority for International Application No. PCT/US17/51224, dated Dec. 1, 2017.

* cited by examiner
† cited by third party

*Primary Examiner* — Tae H Yoon
(74) *Attorney, Agent, or Firm* — Ice Miller LLP

(57)  ABSTRACT

A dental self-adhesive resin cement is provided comprising a two-component system. A first catalyst component includes one or more acidic monomers. A second base component includes one or more basic fillers. The mixture of the first and second components is polymerizable and has an initial pH that is acidic immediately after mixing and a pH of at least about pH 8 after polymerization.

7 Claims, No Drawings

DENTAL SELF-ADHESIVE RESIN CEMENT

This application claims the benefit of U.S. Provisional Application No. 62/397,711, filed Sep. 21, 2016, which is hereby incorporated by reference in its entirety.

BACKGROUND OF THE INVENTION

The invention relates to dental cements and, in particular, to self-adhesive resin cements having a basic pH.

Indirect dental restorations such as inlays, onlays, crowns, bridges and veneers are commonly bonded to the remaining dentin and enamel structure of a tooth using dental cements or luting agents. The cement also seals the interface between the restoration and the tooth to prevent microleakage or the flow of fluids and bacteria into gaps in the interface, which can cause sensitivity, caries, pulpal inflammation or other periodontal disease. The cement may be relatively weak for temporary or provisional restorations, or strongly adhesive for long term retention of permanent restorations.

Conventional dental cements have acidic compositions. Traditional cements include acid-base reaction cements—e.g., zinc oxide cements, zinc phosphate cements, and silicate cements. The acid-base reaction cements are two component systems that typically have a dry powder component generally comprising zinc oxide (and aluminosilicates), mixed with an acidic liquid component such as phosphoric acid or acetic acid. Polycarboxylate cements similarly comprise a dry powder of zinc oxide and polyacrylic acid, mixed with water.

Cements that are more commonly used today are also acidic, such as glass ionomer cements and self-adhesive resin-based cements. Glass ionomer cements generally comprise a fluoroaluminosilicate mixed with an aqueous polyalkenoic acid such as polyacrylic acid. Self-adhesive resin-based cements typically comprise acidic monomers. Non-self-adhesive resin-based cements have neutral pH, but require the tooth surface to be prepared by treatment with acid-etchants and primers to ensure good bonding to the tooth surface. The acidic monomers in the self-etch and self-adhesive resin cements allow the cement composition to be self-etching to promote adhesion.

The acidity of conventional dental cements creates potential problems, such as tooth sensitivity, inhibition of remineralization, and promoting cavity growth. However, it is almost impossible to make a self-adhesive resin cement with a basic pH using the current technology, since all of the current self-adhesive resin cements contain acidic monomers. Dental cements having a basic pH would provide a number of benefits, including promoting remineralization, promoting healing of pulp tissue, inhibiting of bacterial growth, and neutralizing acidic bacterial by-products which may prevent secondary caries. Thus it would be desirable to develop dental cements having basic pH.

SUMMARY OF THE INVENTION

In an embodiment of the invention, a dental self-adhesive resin cement system is disclosed, comprising a polymerizable composition that comprises an acidic monomer and a basic filler. The composition has an acidic pH before polymerization and a basic pH after polymerization.

In another embodiment of the invention, a dental self-adhesive resin cement system is disclosed, comprising a polymerizable composition having a first component and a second component. The first component comprises an acidic monomer and said second component comprises a basic filler. The composition has a pH before polymerization of about pH 4 or less and a pH after polymerization of about pH 8 or more.

In another embodiment of the invention, a dental self-adhesive resin cement system is disclosed, comprising a polymerizable composition having a first component and a second component. The first component comprises an acidic monomer in an amount of about 10-40% by weight of the first component. The second component comprises a basic filler in an amount of about 5-50% by weight of second component. The composition has an acidic pH before polymerization and a basic pH after polymerization.

DETAILED DESCRIPTION OF THE INVENTION

Conventional dental self-adhesive resin cements are one-step systems having acidic compositions that eliminate the need for separate etchants and primers for bonding ceramic and metal indirect restorations to the underlying tooth structure. In contrast to these conventional acidic compositions, self-adhesive resin cements have been developed having compositions with a basic pH.

The basic dental self-adhesive resin cement is a two-component system having a first catalyst component comprising one or more acidic monomers, and a second base component comprising one or more basic or alkaline fillers. The two components are mixed to form a composition that is initially acidic, which facilitates bonding of the cement composition to dental substrates, such as the dentin and enamel of the underlying tooth structure and the ceramic (e.g., zirconia) and/or metal of the restoration. As the cement composition polymerizes, the pH becomes basic. In a preferred embodiment, the cement composition has an initial pH that is acidic immediately after mixing, and preferably has an initial pH of about pH 4 or less. After polymerization, the cement composition preferably has a pH of about pH 8 or more.

In one embodiment, the catalyst component comprises about 50% by weight of the two-component system and the base component comprises about 50% by weight of the two-component system. Additionally, the ratio of the weight percent of one or more acidic monomers in the catalyst component to the weight percent of one or more basic fillers in the base component may range from about 8:1 to about 1:5, with a preferable ratio of acidic monomer weight percent to basic filler weight percent of about 2:1.

In one embodiment, the catalyst component has a composition comprising one or more acidic monomers in an amount of about 10-40 wt %. The acidic monomers may be phosphate monomers, carboxylate monomers, and other acidic monomers that are known in the art. Suitable acidic monomers include: 11-methacryloxy-11-undecadicarboxylic acid (MAC10), bis [2-(methacryloyloxy)ethyl] phosphate (BisMEP), dipentaerythritol penta-acrylate monophosphate (PENTA-P), 10-methacryloxydecyl dihydrogen phosphate (MDP), bis-hydroxyethylmethacrylate ester of biphenyl dicarboxylic anhydride (BPDM), diaryl sulfone dimethacrylate (DSDM), 4-methacryloxyethyl-trimellitic anhydride (4-META), 4-methacryloyloxy ethyl trimellitic acid (4-MET), pyromellitic dianhydride dihydroxyethyl-methacrylate ester (PMDM), pyromellitic dianhydride bis (glycerol dimethacrylate) ester (PMGDM), N-methacryloyl-5-aminosalicylic acid (5-NMSA), methacrylated polyacrylic acid (MPAA), and other acidic monomers known in the art.

The catalyst component may also include one or more additional monomers and/or additives that are known in the art, such as fillers, radiopacifiers, and polymerization initiators. Additional monomers include cross-linking monomers such as dimethacrylate monomers. Suitable additional monomers include bisphenol A glycidylmethacrylate (Bis-GMA), triethylene glycol dimethacrylate (TEGDMA), and urethane dimethacrylate (UDMA). Suitable fillers for the catalyst component include inert glass fillers, such as barium glass, strontium glass, and silica. Nanoparticles such as nano-silica may also be used as fillers to improve the strength and toughness of the resin cement. Radiopacifiers include ytterbium fluoride ($YbF_3$) and zirconia. Various polymerization initiators may be used as are known in the art, such as the photoinitiator camphorquinone (CQ).

In a preferred embodiment, the catalyst component has a composition comprising: about 10-40 wt % acidic monomers, about 10-40 wt % cross-linking monomers, about 20-70 wt % inert glass fillers, about 1-10 wt % nanoparticles, about 2-20 wt % radiopacifiers, and trace amounts of initiator (e.g., about 0.1-2 wt %).

The base component has a composition comprising one or more basic fillers in an amount of about 5-50 wt %. Suitable basic fillers include alkaline powders such as Portland cement, tricalcium silicate, dicalcium silicate, calcium oxide, calcium hydroxide, and other basic fillers that are known in the art.

The base component may also include one or more additional monomers and/or additives that are known in the art, such as fillers, radiopacifiers, and polymerization initiators. These additional monomers and fillers may be of the same type as used in the acidic component. In a preferred embodiment, the base component has a composition comprising: about 5-50 wt % alkaline fillers, about 10-40 wt % dimethacrylate monomers, about 5-50 wt % inert glass fillers, about 1-10 wt % nanoparticles, about 2-20 wt % radiopacifiers, and trace amounts of initiators (e.g., about 0.1-6 wt %).

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

Example 1

The basic self-adhesive resin cement was prepared as a two-component system, comprising a catalyst paste and a base paste having compositions as set forth below. The self-adhesive resin cement comprised of about equal parts of catalyst paste and base paste (i.e., about a 1:1 ratio of catalyst paste and base paste).

TABLE 1

| Catalyst Paste Composition | |
| --- | --- |
| Component | Weight % |
| Glass filler | 62 |
| MDP | 17.2 |

TABLE 1-continued

| Catalyst Paste Composition | |
| --- | --- |
| Component | Weight % |
| DSDM | 8.6 |
| TEGDMA | 11 |
| Tertiary butylperoxybenzoate | 1.2 |

TABLE 2

| Base Paste Composition | |
| --- | --- |
| Component | Weight % |
| Glass filler | 40 |
| Portland Cement III | 12 |
| $YbF_3$ low density | 5 |
| Initiator | 5 |
| ethoxylated Bisphenol A dimethacrylate | 25 |
| BisGMA | 2 |
| TEGDMA | 10 |
| 1,12-dodecanediol dimethacrylate | 1 |

The catalyst and base pastes were mixed to form the basic self-adhesive resin cement, and the pH was tested using a moist pH test strip.

TABLE 3

| pH Over Time | |
| --- | --- |
| Time | pH |
| immediately after mixing | 4 |
| 5 minutes after mixing | 8 (already polymerized) |
| 10 minutes after mixing | 9 (already polymerized) |
| 30 minutes after mixing | 10 (already polymerized) |

The pH of the mixture over time is shown in Table 3. The pH of the basic self-adhesive resin cement system is initially pH 4 immediately after mixing, but increases to pH 8 upon polymerization and continues to become increasingly basic after polymerization.

Example 2

The bond strength of the basic self-adhesive resin cement was tested and compared to conventional acidic self-adhesive dental cements. The basic self-adhesive resin cement was prepared as described in Example 1. The acidic self-adhesive resin cements were obtained commercially and prepared as directed: RelyX® Unicem 2 (3M—St. Paul, Minn.), MaxCem Elite (Kerr Corp.—Orange Calif.), Calibra® Universal (Dentsply—Milford, Del.), NX3 Nexus® (Kerr Corp.—Orange Calif.), and Duo-Link (Bisco—Schaumburg, Ill.).

The bond strength of the resin cements to a zirconia ceramic substrate was measured using the Ultradent® Shear Bond Test Method (Ultradent Prods., Inc.—South Jordan, Utah). The cements were placed on a sandblasted zirconia surface using an Ultradent® jig mold (bonding area 4.5 $mm^2$). The cements were self-cured for 15 min at 37° C., stored in de-ionized water for 24 hours at 37° C., and tested using an Instron® Universal Testing Machine (Instron—Norwood, Mass.) with a crosshead speed of 1 mm/min. The degree of conversion of the monomers in the resin cement compositions was measured by FTIR-ATR up to 30 min at 25° C. in the dark.

TABLE 4

Shear Bond Strength And Degree Of Conversion

| Resin Cement | Product Type | Shear Bond Strength (SD, n = 5) | Deg. of Conversion (SD, n = 3) |
| --- | --- | --- | --- |
| Basic Self-Adhesive Resin Cement | Alkaline | 26.8 MPa (8.9) a | 68.0% (1.5) a |
| RelyX Unicem 2 | Acidic | 16.7 MPa (6.2) ab | 34.3% (7.1) e |
| MaxCem Elite | Acidic | 14.8 MPa (7.3) b | 55.1% (1.9) c |
| Calibra Universal | Acidic | 13.4 MPa (6.5) b | 48.8% (1.4) d |
| NX3 Nexus | Neutral | — | 61.8% (0.7) b |
| Duo-Link | Neutral | — | 66.8% (1.5) a |

The mean values of the shear bond strength and degree of conversion of the resin cements are shown in Table 2. Statistically different values in the same column (p<0.05) are indicated by different letters (a, b, c, d). The basic self-adhesive resin cement was surprisingly found to have significantly greater shear bond strength in comparison to conventional acidic self-adhesive resin cements. Furthermore, the degree of conversion of the monomers in the basic self-adhesive resin cement was found to be greater than in the conventional acidic self-adhesive resin cements, indicating that the presence of the basic fillers did not inhibit or otherwise interfere with polymerization of the resin cement composition.

While particular embodiments of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of this disclosure.

What is claimed is:

1. A dental self-adhesive resin cement system, comprising:
    a polymerizable composition comprising acidic monomers and one or more basic fillers, the acidic monomers in a first component and the basic fillers in a second component, the first and second components in a 1:1 ratio, the acidic monomers in an amount of about 10-40% by weight of the first component, and the ratio of the acidic monomers as a weight percentage of the first component to the basic fillers as a weight percentage of the second component is about 2:1, the basic filler comprising Portland cement, and the acidic monomers comprising 10-methacryloxydecyl dihydrogen phosphate (MDP) and diaryl sulfone dimethacrylate (DSDM);
    wherein the composition has a pH before polymerization of about pH 4 or less and a pH after polymerization of about pH 8 or more.

2. The dental self-adhesive resin cement system of claim 1, wherein the composition further comprises a dimethacrylate monomer selected from the group consisting of: bisphenol A glycidylmethacrylate (BisGMA), triethylene glycol dimethacrylate (TEGDMA), urethane dimethacrylate (UDMA), and combinations thereof.

3. The dental self-adhesive resin cement system of claim 1, wherein the composition further comprises an inert glass filler selected from the group consisting of barium glass, strontium glass, silica, and combinations thereof.

4. The dental self-adhesive resin cement system of claim 1, wherein the composition further comprises a nanoparticle.

5. The dental self-adhesive resin cement system of claim 1, wherein the composition further comprises a radiopacifier selected from the group consisting of:
    ytterbium fluoride ($YbF_3$), zirconia, and combinations thereof.

6. The dental self-adhesive resin cement system of claim 1, wherein the composition further comprises a polymerization initiator.

7. A dental self-adhesive resin cement system, comprising:
    a polymerizable composition comprising acidic monomers and one or more basic fillers, the acidic monomers in a first component and the basic fillers in a second component, the acidic monomers in an amount of about 5-20% by weight of the polymerizable composition, and the ratio of acidic monomers to basic fillers is about 2:1 by weight percent of the polymerizable composition, the basic fillers comprising Portland cement, and the acidic monomers comprising 10-methacryloxydecyl dihydrogen phosphate (MDP) and diaryl sulfone dimethacrylate (DSDM); and
    wherein the composition has an acidic pH before polymerization and a basic pH after polymerization.

* * * * *